(12) United States Patent
McKenna et al.

(10) Patent No.: US 8,334,401 B2
(45) Date of Patent: Dec. 18, 2012

(54) PROCESS FOR THE PRODUCTION OF DIOLS

(75) Inventors: Peter McKenna, Romsey (GB); Mark Smallridge, Hythe (GB); Melissa Matthews, Southampton (GB); Simon Roberts, Romsey (GB)

(73) Assignee: Cognis IP Management GmbH, Duesseldorf (DE)

( * ) Notice: Subject to any disclaimer, the term of this patent is extended or adjusted under 35 U.S.C. 154(b) by 366 days.

(21) Appl. No.: 12/599,771

(22) PCT Filed: May 2, 2008

(86) PCT No.: PCT/EP2008/003540
§ 371 (c)(1),
(2), (4) Date: Nov. 11, 2009

(87) PCT Pub. No.: WO2008/138497
PCT Pub. Date: Nov. 20, 2008

(65) Prior Publication Data
US 2010/0249352 A1    Sep. 30, 2010

(30) Foreign Application Priority Data
May 14, 2007   (DE) .......................... 10 2007 022 521

(51) Int. Cl.
*C07C 69/52*   (2006.01)
(52) U.S. Cl. ...................................... 560/224
(58) Field of Classification Search ........................ None
See application file for complete search history.

(56) References Cited

U.S. PATENT DOCUMENTS

| 3,862,215 | A | * | 1/1975 | Merger et al. ................ 560/189 |
| 4,056,496 | A | * | 11/1977 | Mancini et al. ............... 523/106 |
| 4,075,263 | A | * | 2/1978 | Lane et al. ...................... 525/58 |
| 4,529,787 | A | * | 7/1985 | Schmidt et al. ................ 526/209 |
| 4,724,262 | A | * | 2/1988 | Shimbo et al. ................. 549/222 |
| 6,011,081 | A | | 1/2000 | Benz et al. |
| 6,214,172 | B1 | * | 4/2001 | Groning et al. ................. 203/14 |
| 2006/0258830 | A1 | | 11/2006 | Broell |

FOREIGN PATENT DOCUMENTS

| DE | 10349972 | 5/2005 |
| EP | 1 171 410 B1 | 1/2002 |
| EP | 1 171 411 B1 | 1/2002 |
| EP | 1171410 | 12/2004 |
| EP | 1171411 | 1/2005 |
| GB | 852384 | 10/1960 |
| JP | 3002952 | 1/1988 |
| WO | 00/63149 A1 | 10/2000 |
| WO | 00/63150 A1 | 10/2000 |
| WO | WO-00/63149 | 10/2000 |
| WO | WO-00/63150 | 10/2000 |

OTHER PUBLICATIONS

PCT Written Opinion in PCT/EP2008/003540 of Dec. 7, 2009, 7 pgs.

* cited by examiner

*Primary Examiner* — Johann Richter
*Assistant Examiner* — Clinton Brooks
(74) *Attorney, Agent, or Firm* — Diehl Servilla LLC

(57) ABSTRACT

The invention relates to a process for the production of diols with a special structure which are characterized by formula (I). These diols are substances which, besides two OH groups, contain a C=C double bond so that they are suitable as monomers for the production of polymers. The process comprises hydrolyzing a corresponding cyclic precursor in aqueous medium in the presence of an acid dissolved in that medium, the hydrolysis being accompanied by the elimination of a carbonyl compound, and subsequently neutralizing the acid present in the reaction mixture with a base, the base having a $pK_b$ value above 0.18 and preferably above 3.0 and being present in heterogeneous form.

22 Claims, No Drawings

PROCESS FOR THE PRODUCTION OF DIOLS

CROSS REFERENCE TO RELATED APPLICATIONS

This application is the National Phase entry of PCT/EP2008/003540, filed May 2, 2008 which claims priority to German patent application number 10 2007 022 521.2, filed May 14, 2007 both of which are incorporated herein by reference in their entireties.

FIELD OF THE INVENTION

This invention relates to a process for the production of diols with a special structure which are characterized by formula (I) below. These diols are substances which, besides two OH groups, contain a C=C double bond so that they are suitable as monomers for the production of polymers.

BACKGROUND OF THE INVENTION

Glyceryl monomethacrylate, hereinafter referred to in short as GMMA, can be obtained by hydrolysis of isopropylidene glyceryl methacrylate, hereinafter referred to in short as IPGMA.

GMMA has the following structure (A):

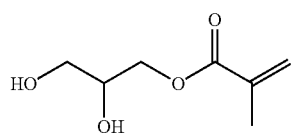

(A)

IPGMA has the following structure (B):

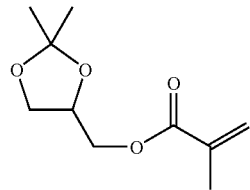

(B)

IPGMA is occasionally abbreviated in the literature to GMAK. Under common nomenclature, IPGMA can also be referred to as (2,2-dimethyl-1,3-dioxolan-4-yl)methyl methacrylate.

GB 852, 384 published in 1960 describes the production of GMMA by hydrolysis of IPGMA, the hydrolysis being carried out in the presence of dilute aqueous solutions of strong mineral acids. Sulfuric acid, hydrochloric acid, nitric acid and phosphoric acid are mentioned as examples of suitable mineral acids. The typical procedure is apparent from Example 1. According to this Example, the sulfuric acid present in the reaction mixture after the hydrolysis of IPGMA was removed by addition of barium hydroxide. Poorly soluble barium sulfate was formed and was removed by filtration. The crude target product GMMA was obtained as a ca. 20% solution in water/acetone (12:1). However, if it was intended to isolate the target product, the solution was saturated with NaCl, extracted with benzene or ether and the organic solvent removed.

Unfortunately, the process known from GB 852,384 has serious disadvantages. Thus, on account of its heavy metal content, the use of barium hydroxide involves a certain risk for ecological and toxicological reasons. The additional use of organic solvents is another unwanted factor. Benzene, which is both inflammable and toxic, is also used as solvent in Examples 2 to 4. It is clear that no neutralization takes place there and that the target product is directly extracted from the acidic aqueous reaction mixture with benzene. In addition to the use of benzene as solvent, this variant has the disadvantage that residual traces of acid in the target product GMMA cannot be ruled out. However, even traces of acid are extremely undesirable because they have a considerable bearing on the stability of GMMA in that they reduce its stability.

In addition, in their own studies based on reproducing Example 1 of GB 852,384, applicants observed the following: if the reaction mixture is neutralized with barium hydroxide and if the water is removed by stripping without extraction using an organic solvent, a GMMA with a high barium content (>1000 ppm) is obtained.

All in all, the method disclosed in GB 852,384 is unsatisfactory, particularly when a high-quality GMMA is required.

Even after twenty years from the GB patent cited above, there had still been no significant breakthrough in the production of GMMA. Thus, in column 4, lines 42 et seq of US-A-4,056,496 published in 1977, there is a reference to GB 852, 384, more particularly to the hydrolysis and to the subsequent procedures disclosed therein. Accordingly, Example 1 of US-A-4,056,496 uses sulfuric acid for hydrolysis and barium hydroxide for neutralization, followed by filtration, addition of NaCl, extraction with benzene or ether and removal of the organic solvent.

And even another 20 years later, Example 1 of US-A-6,011,081 still refers to the "old methods", i.e. to US-A-4,056,496.

High-purity GMMA may be used for various industrial applications, for example as a monomer for the production of polymers for coating purposes, lacquers, paints, adhesives or contact lenses. In the production of contact lenses in particular, GMMA is a technically very important monomer, cf. the art cited in EP-B-1,171,410 B1, page 2, line 6 to page 3, line 19.

The goal of providing high-purity monomers, such as GMMA, is very important above all because even trace impurities can have an extremely negative effect on the one hand during storage of the monomers and, on the other hand, on the quality of polymers produced therefrom. Particularly unwanted impurities in monomers are those which can act as crosslinkers in a polymerization reaction because the presence of crosslinkers during a polymerization reaction prevents and/or inhibits the formation of linear polymers.

Later patents EP-B-1 171 410 B1 and EP-B-1 171 411 B1 describe the production of GMMA by hydrolysis of IPGMA, a key feature of each patent being that the hydrolysis of IPGMA is carried out in the presence of an immobilized acid. According to Example 1 of EP-B-1 171 410 B1, IPGMA, deionized water and a cation exchanger are introduced into a reaction vessel and an air stream is passed 48 h through the mixture for the purpose of agitation. A disadvantage of the process described in these patents is that, through the passage of an air stream during the hydrolysis, the acidic ion exchanger undergoes serious erosion which is unacceptable where product purity has to meet stringent requirements and which cannot be completely removed even by subsequent filtration.

For the rest, several other disadvantages of the prior art represented by the PCT equivalents to EP-B-1 171 410 B1 and EP-B-1 171 411 B1 (namely WO 00/63149 and WO 00/63150) are mentioned in DE-A-103 49 972 (cf. page 2, paragraph [0007] and paragraph [0009]).

The technique of hydrolysis in the presence of an acidic ion exchanger is also described in later application DE-A-103 49 972 A1, although the process described therein does have to be carried out continuously. The reaction is carried out in a fixed bed and the carbonyl compound released by hydrolysis is continuously removed from the reaction medium.

DETAILED DESCRIPTION OF PREFERRED EMBODIMENTS

The problem addressed by the present invention was to provide a process for the production of polymerizable monomers corresponding to formula (I) below which would not have the disadvantages of the prior art. More particularly, the process should lead to compounds (I) of high purity and would be particularly suitable for the production of GMMA from IPGMA. The compounds (I) should be useful for the production of contact lenses. The process should therefore lead to compounds (I) with very low acidity content, which is important as it reduces the likelihood of protein and lipid deposition on contact lenses.

The present invention relates to a process for the production of polymerizable monomers corresponding to formula (I):

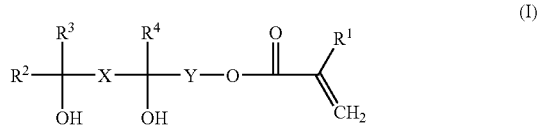

(I)

in which the substituent $R^1$ is hydrogen or a $C_{1-4}$ alkyl group, the substituents $R^2$ to $R^4$ independently of one another represent hydrogen or an aliphatic, cycloaliphatic or aromatic radical, the substituent X is a group —$(CH_2)_n$— and n is the number 0 or 1, the substituent Y is a group —$(CHR^5)_m$— and m is the number 0, 1 or 2 and the substituent $R^5$ is hydrogen or an OH group characterized in that it comprises the steps of hydrolyzing a compound corresponding to formula (II):

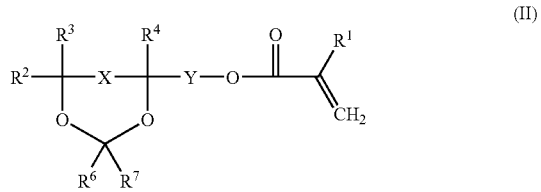

(II)

in which the substituents $R^1$, $R^2$ to $R^4$, X and Y are as defined above and the substituents $R^6$ and $R^7$ independently of one another represent hydrogen or an aliphatic group, in aqueous medium and in the presence of an acid dissolved in the aqueous medium, the hydrolysis being accompanied by elimination of a compound (III):

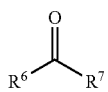

(III)

in which $R^6$ and $R^7$ are as defined above, and contacting the mixture obtained with a weak base to neutralize the acid present in the mixture, the base having a $pK_b$ value above 0.18 and being present in heterogeneous form.

In a particularly preferred embodiment of the process according to the invention, the base used must have a $pK_b$ value above 3.0.

The neutralization of the acid present in the mixture is a key feature of the process according to the invention. As mentioned above, a base is used for this purpose, this base having a $pK_b$ value above 0.18 and being present in heterogeneous form. By "present in heterogeneous form" is meant that the base is not dissolved in water, but is present in solid form. In a preferred embodiment, the base is used in immobilized form, by which is meant that the base is applied to the outer and/or inner surface of solid water-insoluble particles and may be physically and/or chemically bound to those surfaces. In a most particularly preferred embodiment of the process according to the invention, basic ion exchange resins may be used as the bases.

The feature that the base must have a $pK_b$ value above 0.18 is explained in the following. The importance of $pK_b$ values is known among experts. They are a measure of the ability of bases to bind protons and relate to the following equilibrium reaction:

$$H_2O(1) + B(eq) \leftrightarrow BH^+(eq) + OH^-(eq)$$

In this equation, B is a base. The equation describes the equilibrium reaction between the base and water, the base taking up protons at its own intrinsic rate and changing into the protonated form $BH^+$ in the process and, because the proton taken up by the base emanates from the water, the proton logically changing into the form $OH^-$. Since $pK_b$ values are normally quoted for 25° C., the same applies for the present invention. Lithium hydroxide has a $pK_b$ value of 0.18. Accordingly, the above statement that the base used in the process according to the invention must have a $pK_b$ value above 0.18 means that this base is weaker than lithium hydroxide.

In addition, reference is made to the fact well-known to the expert that some bases can have several $pK_b$ values. One example of such a base is lead hydroxide, $Pb(OH)_2$, for which the values $pK_{b1}$ (3.02) and $pK_{b2}$ (7.5) are quoted in the literature. Another example of such a base is ethylenediamine for which the values $pK_{b1}$ (4.07) and $pK_{b2}$ (7.15) are quoted in the literature. The same applies, for example, to piperazine which is characterized by the values $pK_{b1}$ (4.19) and $pK_{b2}$ (8.45). It is pointed out that the examples just mentioned for bases with several $pK_b$ values are merely intended to illustrate the principle under discussion here.

In cases where a base having more than one $pK_b$ value by virtue of its special structure is used, the $pK_b$ value for the base defined above for the process according to the invention (>0.18 and preferably >3.0) means that what is understood by the $pK_b$ value is the $pK_{b1}$ value.

As mentioned above, basic ion exchange resins are preferably used in the process according to the invention. It is pointed out in this regard that manufacturers of such resins typically cite $pK_a$ values for such resins. Since the relationship between $pK_a$ and $pK_b$ is as follows:

$$pK_a + pK_b = 14$$

the $pK_b$ value can easily be calculated from this equation. For example, the ion exchange resin "Amberlyst A21" has a $pK_a$ value according to the manufacturer of 8.5, which means that it has a $pK_b$ value of 5.5 ($pK_b=14-pK_a$). Or, the $pK_b$ value for "Amberlyst A24", which has a $pK_a$ value of 9.5, works out at 4.5.

A preferred embodiment of the process according to the invention is characterized by the use of a (weak) basic ion exchange resin which contains amine functions, more particularly tertiary amine functions.

Examples of suitable basic ion exchange resins are (1) Amberlite IRA96RF, Amberlyst A21, Amberlyst A23 and Amberlyst A24 from Rohm & Haas and (2) Dowex 66, Dowex Monosphere 66, Dowex Monosphere 77, Dowex Marathon WBA, Dowex Marathon WBA-2, Dowex UPCORE Mono WB-500, XUS 43594.00, Dowex M-43 and Dowex M4195 from Dow. With the exception of Dowex M 4195, the basic ion exchange resins mentioned are all based on tertiary amines.

In one embodiment,
$R^1$ is hydrogen or a methyl group,
the substituents $R^2$, $R^3$ and $R^4$ represent hydrogen,
X is a group $-(CH_2)_n$ and n is the number 0,
Y is a group $-(CH_2)_m$ and m is the number 1.
In another embodiment,
$R^1$ is a methyl group,
the substituents $R^2$, $R^3$ and $R^4$ represent hydrogen,
X is a group $-(CH_2)_n$ and n is the number 0,
Y is a group $-(CH_2)_m$ and m is the number 1 and
the substituents $R^6$ and $R^7$ are methyl groups.

It is readily apparent that, in this embodiment, compound (II) is IPGMA, compound (III) is acetone and compound (I) is GMMA.

A mineral acid selected from the group consisting of sulfuric acid, hydrochloric add and hydrobromic acid is preferably used as the acid in the hydrolysis step of the process according to the invention.

In one embodiment of the process according to the invention, a gas stream is passed through the reaction mixture during the hydrolysis step in order to remove compound (III) released from the reaction mixture. The gas used is preferably air. In this case, the hydrolysis is preferably carried out by the continuous introduction of water at a constant volume.

In one embodiment of the process according to the invention, the compound (II) is hydrolyzed in the presence of an inhibitor. Basically, the nature of the inhibitor is not critical. Hydroquinone monomethyl ether (MEHQ) is preferably used as the inhibitor.

In a preferred embodiment of the process according to the invention, the hydrolysis step is carried out in the absence of organic solvents.

In another embodiment of the process according to the invention, the neutralization step is followed by filtration. The aqueous solution of (I) obtained after the filtration is freed from water by stripping, preferably using a film evaporator or a tube evaporator. Preferred types of film evaporators are thin film evaporators, e.g. rotary evaporators or wiped film evaporators. Preferred types of tube evaporators are falling film evaporators or rising film evaporators.

The neutralization step of the process according to the invention may be carried out discontinuously (in batches) or continuously.

The present invention also relates to the use of the monomers (I) obtainable by the process according to the invention for the production of polymers, more particularly polymers used for medical applications, for example for instruments and equipment in the field of opthalmology, implants, prostheses and hydrogel articles.

The monomers (I) obtainable by the process according to the invention are preferably used for the production of contact lenses where they may be used as sole monomer or in combination with other comonomers. By contact lenses are meant both hard and soft contact lenses.

The present invention also relates to a process for the production of polymers based on one or more monomers (I) obtainable by the process according to the invention and, optionally, one or more comonomers. The polymers are preferably polymers used for medical applications, for example for instruments and equipment in the field of ophthalmology, implants, prostheses and hydrogel articles and, more particularly, hard or soft contact lenses. In principle, such polymers can be produced by any of the relevant methods known to the expert. All the usual auxiliaries and additives may also be used. Examples of suitable additives are those described in EP-B-1 171 410, page 7, lines 8-12 which are incorporated herein by reference. Examples of suitable surfactants and dispersants are those described in EP-B-1 714 410, page 7, lines 13-20 which are incorporated herein by reference. Examples of suitable comonomers are those described in EP-B-1 171 410, page 7, line 26 to page 8, line 16 which are incorporated herein by reference.

EXAMPLES

Example 1

27.0 kg of Isopropylidene glyceryl methacrylate containing 80 ppm MEHQ (the IPGMA had been obtained by transesterification of methyl methacrylate and 2,2-dimethyl-4-hydroxymethyl-1,3-dioxolane) and 17.8 kg demineralized water were charged into a reactor equipped with an air sparge. The reaction mixture was stirred while an air stream was passed through (10 litres per minute). 77 g of a 10% by weight aqueous hydrochloric acid were added and the reaction was continued at 20° C. The loss of water caused by the air stream in the reactor was compensated by the continuous addition of water so that the reaction was carried out at constant volume. The reaction was continued until the IPGMA content of the reaction mixture was below 0.16% by weight. The reaction time required to that end was 48 hours.

To remove excess acid, the reaction mixture was neutralized by addition of 1.9 kg Amberlyst A24 (basic ion exchange resin commercially available from Rohm & Haas), the ion exchange resin having been freshly washed beforehand with deionized water). The suspension was stirred for 1 hour, after which the acidity was below 0.05 mg KOH/g. The suspension was then filtered, an aqueous solution of GMMA being obtained.

The water present in this aqueous GMMA solution was removed by stripping using a wiped film evaporator (a standard 1/100 system from Lab-Plant Distillation Systems). The main column had an internal diameter of 100 mm, the heated length was 480 mm and the heated surface 0.15 m². The aqueous GMMA solution was delivered to the distillation unit via a preheater adjusted to a temperature of 40° C. in a quantity of 800 g/h. The walls of the evaporator were heated to a temperature of 60° C. The aqueous GMMA solution was stripped in 3 passes, the vacuum being lowered from 50 mbar to 10 mbar. A high-purity GMMA was obtained in this way and was characterized as follows:

water content below 1% by weight
glyceryl dimethacrylate (GDMA) content below 0.06% by weight.
methacrylic acid content below 0.02%

What is claimed is:

1. A process for the production of polymerizable monomers corresponding to formula (I):

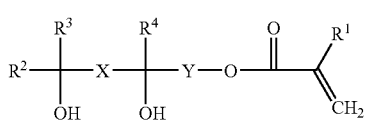

in which the substituent $R^1$ is hydrogen or a $C_{1-4}$ alkyl group,
$R^2$ to $R^4$ independently represent hydrogen or an aliphatic, cycloaliphatic or aromatic moiety,
X is a group $-(CH_2)_n$ and n is the number 0 or 1,
Y is a group $-(CHR^5)_m$, and m is the number 0, 1 or 2, and $R^5$ is hydrogen or an OH group, the process comprising the steps of:

(a). hydrolyzing a compound corresponding to formula (II):

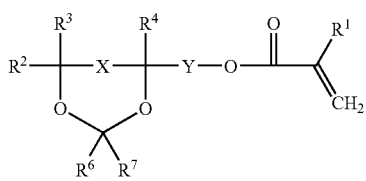

in which the substituents $R^1$, $R^2$ to $R^4$, X and Y are as defined above and the substituents
$R^6$ and $R^7$ independently represent hydrogen or an aliphatic group,
in aqueous medium and in the presence of an acid dissolved in the aqueous medium to form a mixture, the hydrolysis being accompanied by elimination of a compound (III):

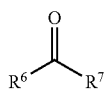

in which $R^6$ and $R^7$ are as defined above, and (b) contacting said mixture with a weak base to neutralize the acid present in the mixture, said base having a $pK_b$ value above 0.18 and being present in heterogeneous form.

2. The process as claimed in claim 1 wherein said base has a $pK_b$ value above 3.0 and is present in heterogeneous form.

3. The process as claimed in claim 2 wherein said base is in an immobilized form.

4. The process as claimed in claim 3 wherein said base comprises a basic ion exchange resin.

5. The process of claim 1 wherein $R^1$ is hydrogen or a methyl group, $R^2$, $R^3$ and $R^4$ represent hydrogen, X is a group $-(CH_2)_n$ and n is the number 0, and Y is a group $-(CH_2)_m$ and m is the number 1.

6. The process of claim 5 wherein $R^1$ is a methyl group and $R^6$ and $R^7$ are methyl groups.

7. The process of claim 1 wherein said acid comprises a mineral acid.

8. The process as claimed in claim 7, wherein said mineral acid is selected from the group consisting of sulfuric acid, hydrochloric acid and hydrobromic acid.

9. The process of claim 4 wherein said basic ion exchange resin contains amine functions.

10. The process as claimed in claim 9 wherein said amine functions comprise tertiary amines.

11. The process as claimed in claim 10 wherein said basic ion exchange resin is selected from the group consisting of Amberlite IRA96RF, Amberlyst A21, Amberlyst A23, Amberlyst A24, Dowex 66, Dowex Monosphere 66, Dowex Monosphere 77, Dowex Marathon WBA, Dowex Marathon WBA-2, Dowex UPCORE Mono WB-500, XUS 43594.00 and Dowex M-43.

12. The process of claim 1 wherein a gas stream is passed through the mixture during the hydrolysis step to remove the compound (III) released from the reaction mixture.

13. The process as claimed in claim 12 wherein said gas is air.

14. The process as claimed in claim 12 wherein the hydrolysis step is carried out by continuous introduction of water at a constant volume.

15. The process of claim 1 wherein compound (II) is hydrolyzed in the presence of an inhibitor.

16. The process as claimed in claim 15 wherein said inhibitor comprises hydroquinone monomethyl ether (MEHQ).

17. The process of claim 1 wherein the hydrolysis is carried out in the absence of organic solvents.

18. The process of claim 1 wherein the neutralization step is followed by filtration.

19. The process as claimed in claim 18 wherein the aqueous solution of (I) obtained after filtration is freed from water by stripping.

20. The process as claimed in claim 19 wherein a thin film evaporator is used for said stripping.

21. The process of claim 1 wherein the neutralization step is carried out discontinuously.

22. The process of claim 1 wherein the neutralization step is carried out continuously.

* * * * *